United States Patent [19]
Rayhack et al.

[11] Patent Number: 6,007,535
[45] Date of Patent: Dec. 28, 1999

[54] MULTI-PLANE BONE DISTRACTION SYSTEM

[75] Inventors: John M. Rayhack, 13914 Shady Shores Dr., Tampa, Fla. 33613; Daniel A. Perkins, Hyde Park, Utah

[73] Assignee: John M. Rayhack, Tampa, Fla.

[21] Appl. No.: 08/969,054

[22] Filed: Nov. 12, 1997

Related U.S. Application Data

[63] Continuation-in-part of application No. 08/582,523, Jan. 3, 1996, abandoned.
[51] Int. Cl.$^6$ ............................ A61B 17/60; A61B 17/56; A61B 17/58
[52] U.S. Cl. ................................ 606/57; 606/69; 606/71; 606/87; 606/96; 606/105
[58] Field of Search ................................ 606/53, 54, 57, 606/58, 59, 69, 70, 71, 80, 82, 86, 87, 88, 96, 97, 98, 102, 104, 105, 79

[56] References Cited

U.S. PATENT DOCUMENTS

| 4,096,857 | 6/1978 | Cramer et al. ............................ 606/86 |
| 5,403,322 | 4/1995 | Herzenberg et al. ...................... 606/98 |

OTHER PUBLICATIONS

Rayhack Radial Malunion Distraction System: Surgical Protocol, 1997.

*Primary Examiner*—Michael Buiz
*Assistant Examiner*—Julian W. Woo
*Attorney, Agent, or Firm*—Stein, Schifino & Van Der Wall

[57] ABSTRACT

A multi-plane bone distraction system including a saw guide, a drill guide, a rigid plate and a distraction assembly for use as a distraction device in cutting and lengthening the bone or as a compression device in cutting and shortening the bone in conjunction with repositioning the other end of the bone in three planes relative to the one end of the bone.

41 Claims, 12 Drawing Sheets

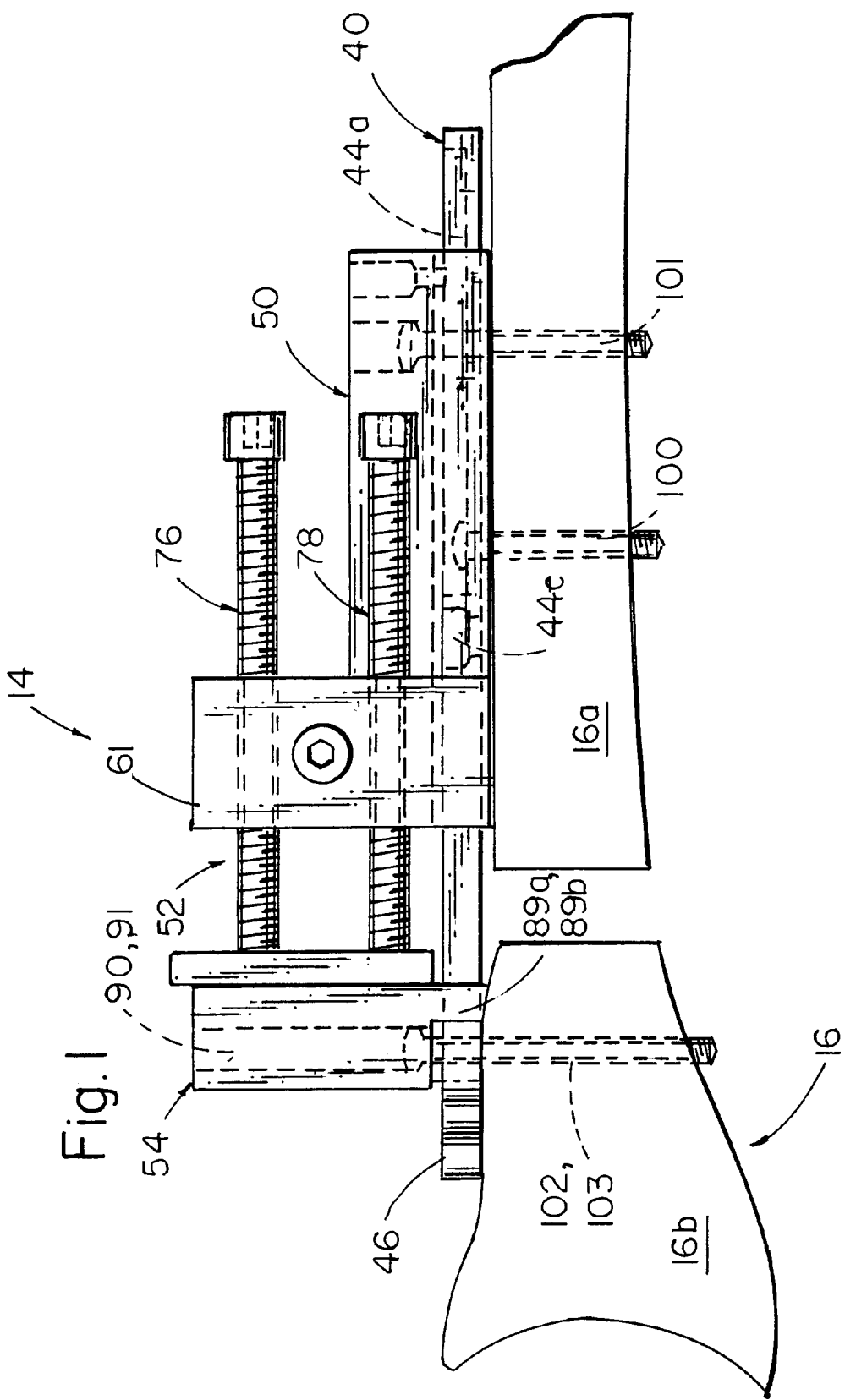

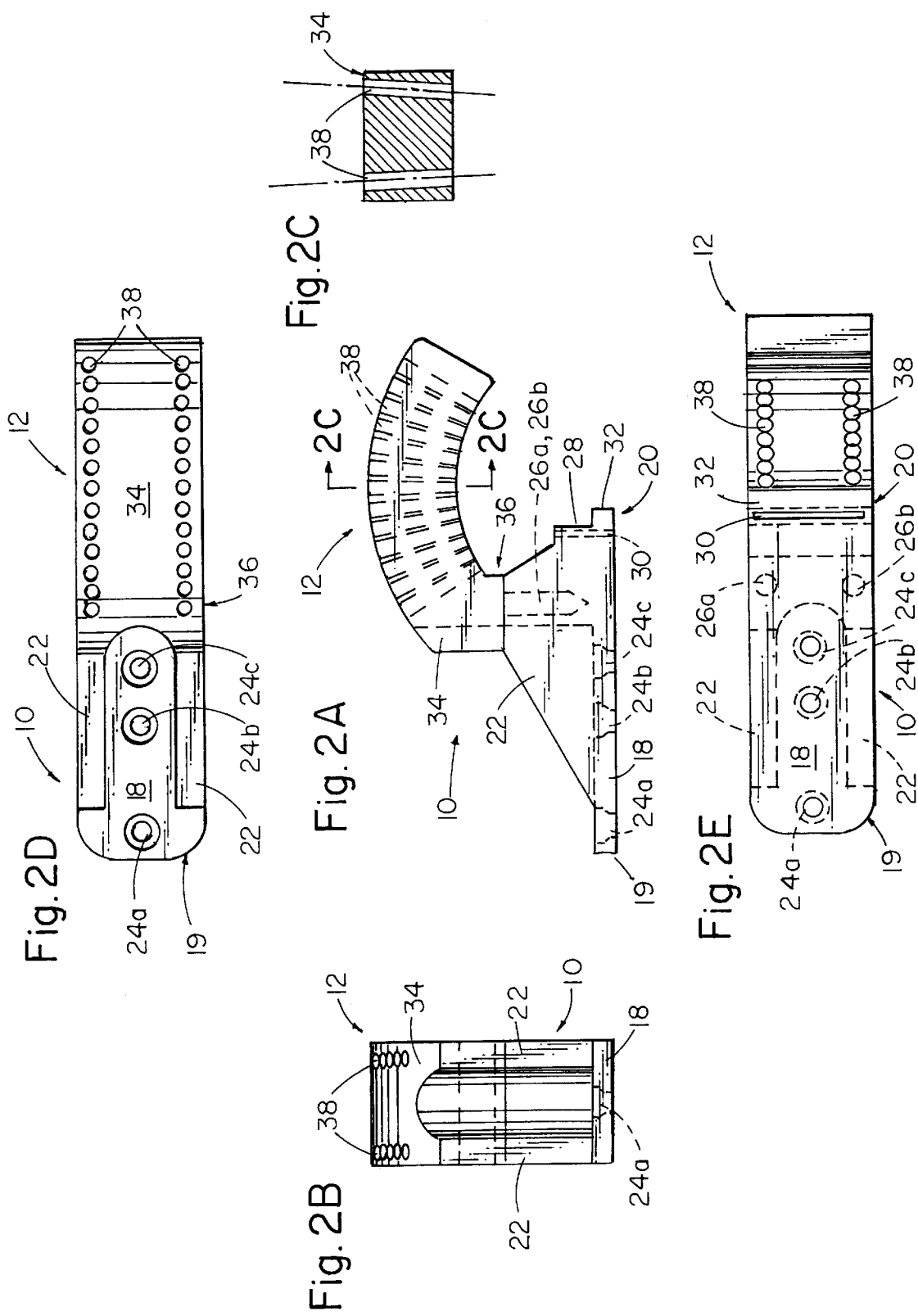

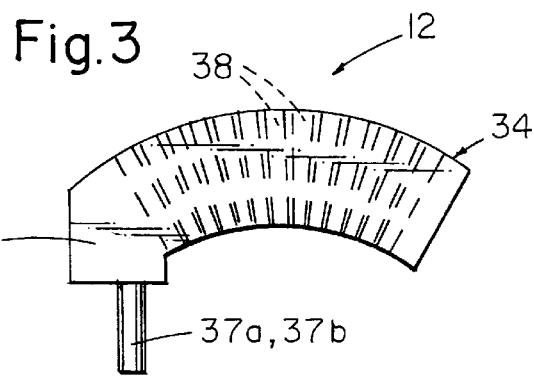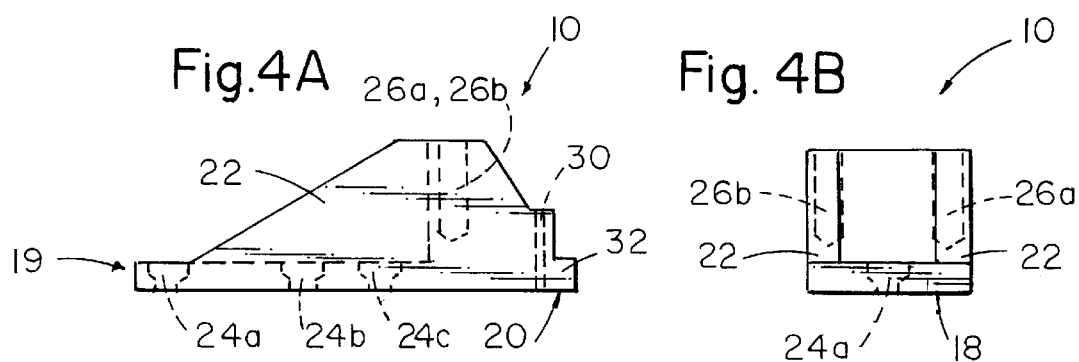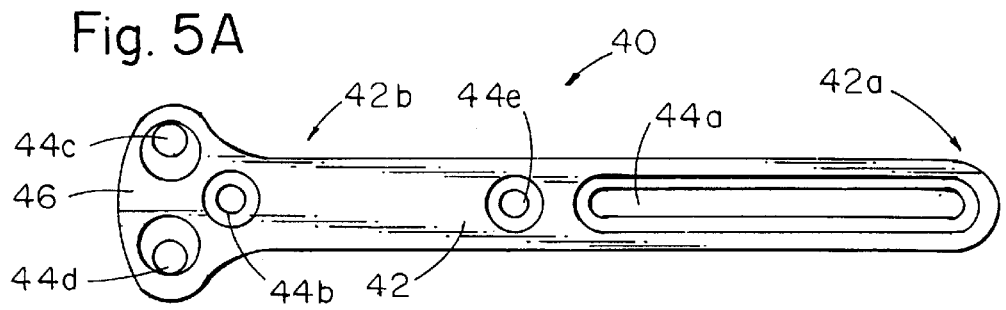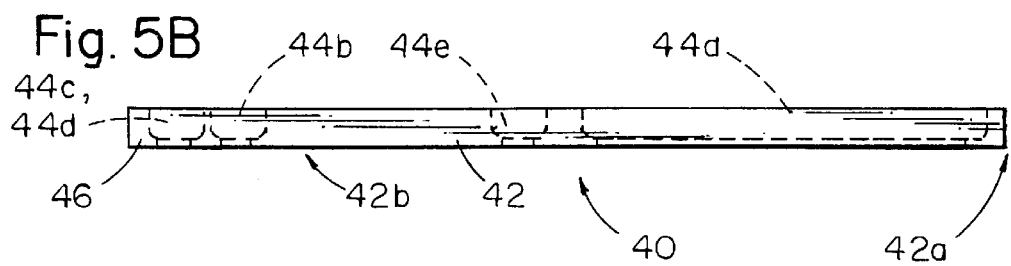

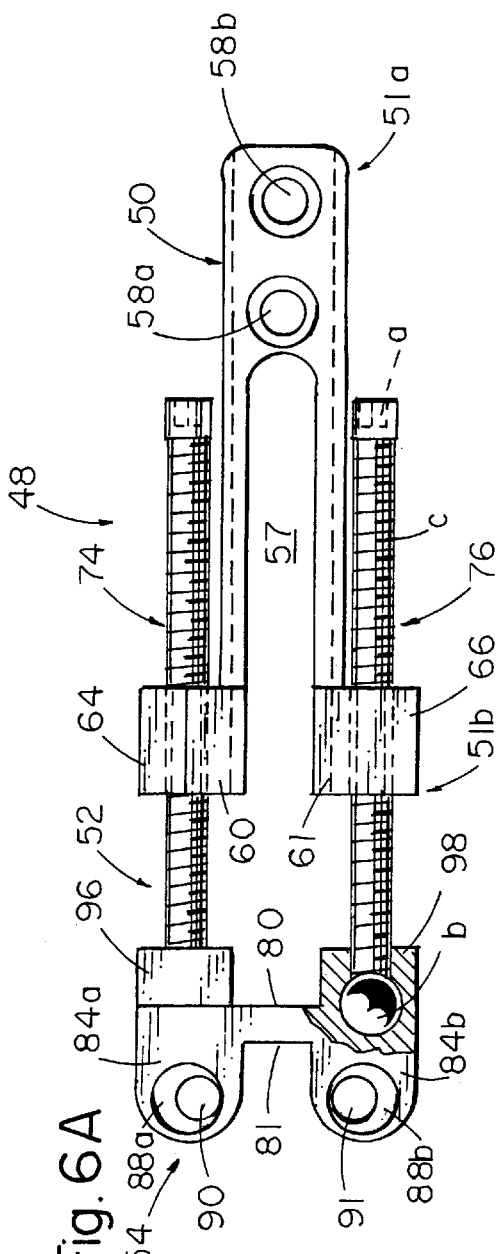

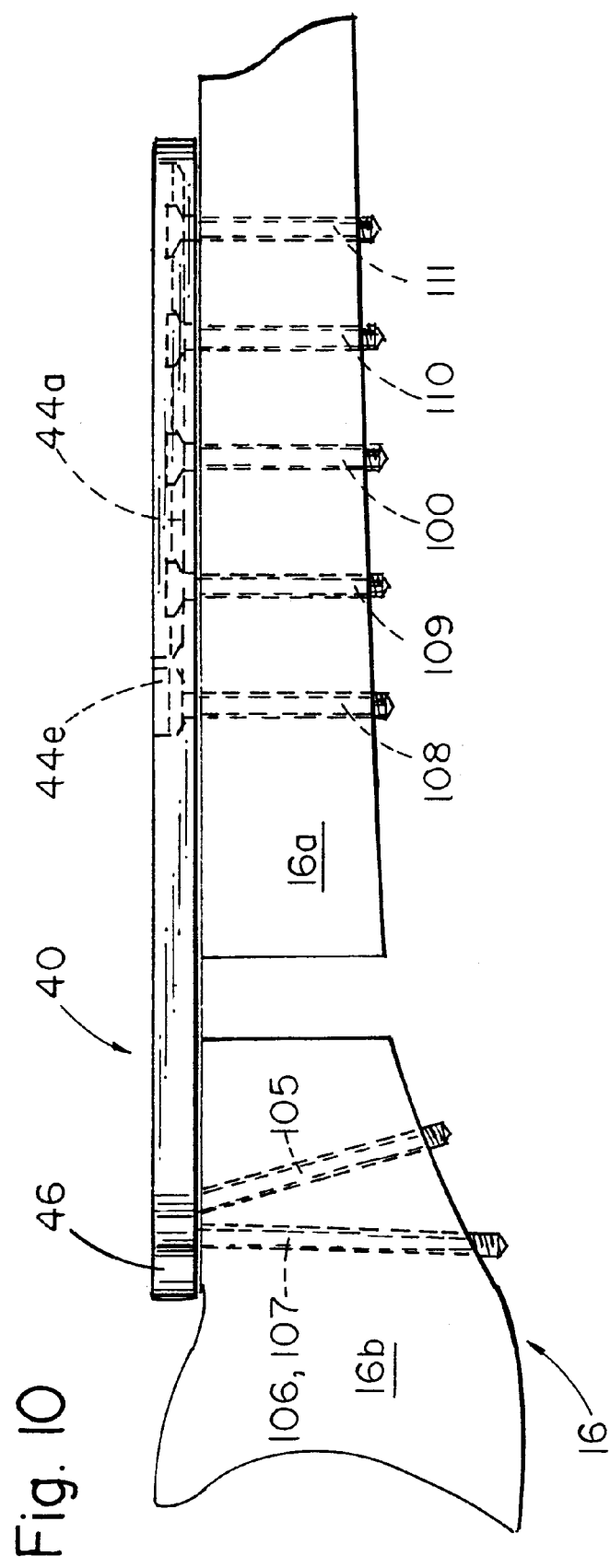

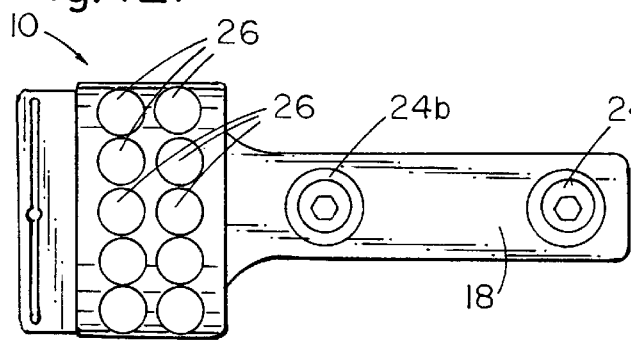
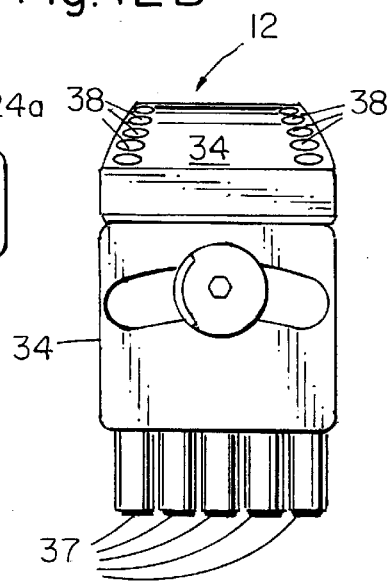
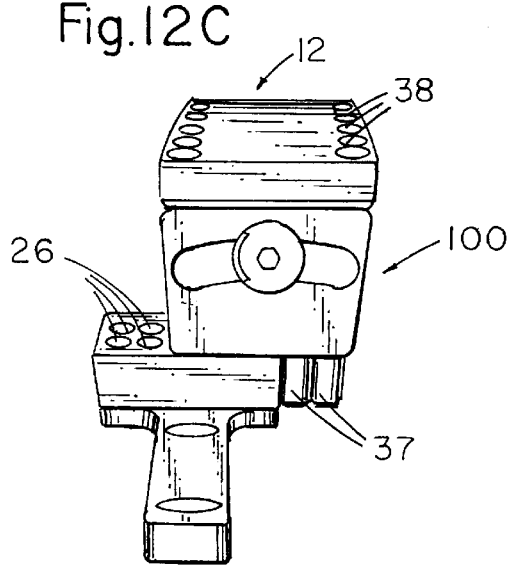
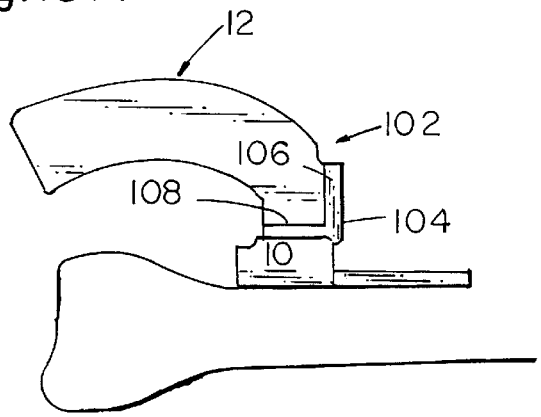

MULTI-PLANE BONE DISTRACTION SYSTEM

This is a continuation-in-part of application Ser. No. 08/582,523, now abandoned.

BACKGROUND OF THE INVENTION

1. Field of the Invention

This invention relates to a bone distraction system and, more particularly, to a multi-plane bone distraction system for providing the ability to distract and reposition bone ends relative to three planes.

2. Description of the Background Art

Presently, there exists numerous types of bone compression devices in which the ends of a fractured or cut bone are forced together by an adjustment assembly where, after operation of the adjustment assembly, a permanent or temporary rigid plate is affixed to securely retain the ends of the cut bone together. Of the numerous types of distraction devices available today throughout the industry, some allow for the lengthening of the bone by distracting the ends of the bones apart by a desired distance and securing the ends of the bone at the desired distance while inserting a bone segment in the gap between the ends of the bone to facilitate the growth of the bone across the gap. Additionally, some of the current designs are to be used both as a compression and a distraction device. Representative compression/distraction devices for use in osteotomy procedures are disclosed in U.S. Pat. Nos. 5,147,358, 5,364,396, 3,244,170, 3,604,414, 4,475,546, 4,187,841, 3,709,219, 2,333,033, and 4,929,247. Additionally, the following foreign patents disclose various embodiments of distraction devices such as EU No. 747,876, DL No. 206,074 and FR. No. 1,507,627. Further, U.S. Pat. Nos. 5,219,349, 5,192,321, 5,176,685, 5,129,909 and 5,042,983 disclose various embodiments of relevant fixators and bone cutting devices. The disclosures of the above-listed patents are hereby incorporated by reference herein.

Of the patents listed above, the East German Patent Number 206,074, the French Patent Number 1,507,627 and the U.S. Pat. No. 3,244,170 disclose similar bone compression devices that are to be used in combination with a slotted plate. However, disadvantages are noted in the above-referenced bone compression and distraction devices. First, many of the patents disclose devices utilizing bone screws that engage only through one cortex of the bone. Further, the means for adjustment in the above-referenced patents are generally positioned substantially off-axis from the longitudinal axis of the bone that is being compressed or distracted thereby increasing the potential for bending or toggling of the bone screw to occur during the use of excessive force in the adjustment means. This would further result in the weakening of the adjustment assembly's connection to the bone. Further, the adjustment assembly's use of a pin (French Patent) or a claw (Germany Patent) may result in scoring of the slotted plate should the pin or claw slip during use. The scoring of the plate could then result in crevice corrosion.

As to many of the devices disclosed in the above-referenced patents, some do not provide for both compression and distraction of a bone. When both compression and distraction capabilities are not present in the device, the inserting of a bone segment in order to lengthen the bone becomes difficult since the ends of the bone cannot be compressed to retain the bone segment therebetween. As well, recutting or reshaping of the ends of the bones is difficult to accomplish without having both distraction and compression capabilities.

Furthermore, and most importantly, none of the above-referenced patents have the ability to distract, compress and reposition in multi-planes, (three distinct planes). Thus, all of the above-referenced devices provide for only linear distraction and compression of the ends of the bones. None of the above-referenced patents disclose devices that provide for angular adjustment or repositioning of one end of the bone relative to the other end of the bone. Thus, the correction of malunions and abnormal curvatures in bones occurring due to abnormal bone growth is not provided for in the prior art.

Therefore, it is an object of this invention to provide an improvement which overcomes the aforementioned inadequacies of the prior art devices and provides an improvement which is a significant contribution to the advancement of the bone distraction and compression art.

Another object of this invention is to provide a new and improved multi-plane bone distraction system that provides for compression, distraction and repositioning in three distinct planes, the multi-plane repositioning capability thereby allowing for angular adjustments to be made.

Another object of this invention is to provide a multi-plane bone distraction system that allows for the removal of a bone segment from a malunion of a bone whereby the other end of the bone can be realigned in a proper position.

Another object of this invention is to provide a multi-plane bone distraction system that allows for the separating of the other end of the bone from the proximal end for bone grafting to be initiated therein.

Another object of this invention is to provide a multi-plane bone distraction system that utilizes a rigid plate to be left on the bone after operation of the distraction device, the rigid plate having a three-point attachment at the other end so to secure the other end of the bone in any rotated linear or non-linear position.

Another object of this invention is to provide a multi-plane bone distraction system that utilizes a saw guide for controlling the angle of sawing and sawing location on the bone, the saw guide thereby assuring a consistent cut at a safe and advantageous position away from the other end of the bone.

Another object of this invention is to provide a multi-plane bone distraction system that utilizes a drill guide for controlling the angle of drilling and the exact location to drill on the other end of the bone.

Another object of this invention is to provide a multi-plane bone distraction system for use in distracting ends of a bone and controlling the alignment thereof in three planes, the multi-plane bone distraction system comprising in combination: a saw guide means for controlling the angle of sawing and sawing location on the bone, the saw guide means being releasably secured in position on the one end of the bone; a drill guide means for controlling the location and angle of drilling to apply to the other end of the bone, the drill guide means being coupled to the second end of the saw guide means and thereby extending outward from the saw guide means over the other end of the bone; a multi-plane distraction means for distracting and repositioning the other end of the bone in three planes from the one end of the bone to facilitate repairing of the bone, the multi-plane distraction means being coupled to the one end and the other end of the bone after the saw guide means and the drill guide means are removed from releasably secured positioning on the one end of the bone, whereby the saw guide means and the drill guide means may be positioned on the bone to facilitate the sawing and drilling of the bone and thereafter be removed and the multi-plane distraction means may be correspondingly positioned on the bone and operated allowing the other end of the bone to be distracted and repositioned in three planes relative to the one end of the bone.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a more comprehensive understanding of the invention may be obtained by referring to the summary of the invention, and the detailed description of the preferred embodiment in addition to the scope of the invention defined by the claims taken in conjunction with the accompanying drawings.

SUMMARY OF THE INVENTION

The invention is defined by the appended claims with the specific embodiment shown in the attached drawings. For the purposes of summarizing this invention, this invention comprises a saw guide, a drill guide, a rigid plate and a distraction assembly. The saw guide is comprised of a base structure that is releasably secured in position on one end of the bone, and an integral wall extending outward from the second end forming a transverse slot that facilitates the guided sawing of the bone. Once the saw guide is releasably secured in position on the one end of the bone, the drill guide is coupled to the second end of the saw guide such that the drill guide extends outward from the saw guide over the other end of the bone.

The drill guide is comprised of a main body having a mounting end and a multiplicity of drill holes angularly aligned in two planes therein to facilitate the guided drilling of the other end of the bone prior to sawing. The drill holes are spaced apart at a fixed incremental angle such that a specific set of holes are used for the specific amount of angled volar or dorsal tilt that is required for correction and the amount of angled tilt to assure proper fixation. The drill guide may include a supination and pronation connection assembly and/or a medial and lateral translation assembly for providing supination/pronation and/or medial/lateral adjustments.

After utilizing the saw guide and drill guide and subsequently removing them, the rigid plate and distraction assembly are secured in position on the one end of the bone. The rigid plate is comprised of an elongated member having a proximal end, a distal end, a first securing hole positioned adjacent the proximal end, and an enlarged head coupled to the distal end. The first securing hole is in the form of a slotted hole which receives a first bone screw therethrough and facilitates the slidable movement of the rigid plate relative to the first bone screw. The rigid plate is positioned on the bone such that the proximal end of the rigid plate is positioned on the one end of the bone and the enlarged head is positioned on the other end of the bone.

The distraction assembly is comprised of a base frame having one end, an opposite end, a slot positioned centrally therebetween, an adjustment head having a first and a second recessed screw hole, and a multi-plane adjustment means for adjustably interconnecting the adjustment head to the base frame. The base frame, being seated on the rigid plate, is releasably secured to the one end of the bone. The adjustment head is releasably secured to the other end of the bone via the holes previously drilled with the drill guide. The adjustment means is then operated to thereby adjust the adjustment head relative to the base frame so as to reposition the other end of the bone relative to the one end of the bone. While distracting and adjusting the distraction assembly, the rigid plate slides along the longitudinal axis of the bone in accordance with the adjustment being made. The rigid plate is then secured in position on both the one end and the other end of the bone whereupon the distraction assembly is then removed from the bone. After completing operation of the distraction assembly, the rigid plate is left alone in position fixedly securing the one end and the other end of the bone in the desired correct alignment wherein future growth of the bone can overtake the gap and the alignment will be retained.

The multi-plane adjustment means is comprised of a first, a second and a third adjustment screw wherein each of the adjustment screws have a head portion, a ball member and a threaded shaft therebetween. The first, second and third adjustment screws interconnect the base frame and the adjustment head such that individually adjusting one adjustment screw relative to the other adjustment screws serves to gradually rotate the adjustment head in response. A rotating of the adjustment screws clockwise serves to push out on the adjustment head and a rotating of the adjustment screws counterclockwise serves to pull inward on the adjustment head. The first, second and third adjustment screws are individually adjusted incrementally until the desired distance and desired realignment angle are achieved.

Upon completing the adjustment of the distraction assembly, the rigid plate is secured to the one end and the other end of the bone by way of bone screws that are threaded into both cortices of the bone.

The multi-plane bone distraction system of the present invention may be used as a distraction device in cutting and lengthening the bone or as a compression device in cutting and shortening the bone in conjunction with repositioning the other end of the bone in three planes relative to the one end of the bone.

An important feature of the present invention is that a multi-plane repositioning of the other end of a bone to the one end is provided for in conjunction with a compression/distraction of the bone as is required in the repairing of malunions or fractures occurring in the radius or other bones.

Another important feature of the present invention is that a rigid plate is utilized so as to cooperate with the distraction assembly and facilitate rigidly securing the other end of the bone relative to the one end of the bone in its repositioned state.

Another important feature of the present invention is that the separating of the other end of the bone from the one end of the bone is provided for wherein a bone segment may be inserted therebetween or removed therefrom so to facilitate the repairing of the bone.

The foregoing has outlined rather broadly, the more pertinent and important features of the present invention. The detailed description of the invention that follows is offered so that the present contribution to the art can be more fully appreciated. Additional features of the invention will be described hereinafter. These form the subject of the claims of the invention. It should be appreciated by those skilled in the art that the conception and the disclosed specific embodiment may be readily utilized as a basis for modifying or designing other methods and structures for carrying out the same purposes of the present invention. It should also be realized by those skilled in the art that such equivalent methods and structures do not depart from the spirit and scope of the invention as set forth in the appended claims.

BRIEF DESCRIPTION OF THE DRAWINGS

For a more succinct understanding of the nature and objects of the invention, reference should be directed to the following detailed description taken in conjunction with the accompanying drawings in which:

FIG. 1 is a side elevational view of the distraction assembly in position seated on the rigid plate having the base frame and the adjustment head secured to the one end and the other end of the bone, the distraction assembly having been operated so to separate the ends of the bone;

FIGS. 2A and 2B are various side views illustrating the saw guide and drill guide in their coupled state wherein the first, second and third screw holes, the transverse slot, the spacer and the multiplicity of drill holes angularly aligned in their relative positions to each other;

FIG. 2C is a cross-sectional view taken along line A—A illustrating the drill holes extending through the drill guide;

FIG. 2D is a top view of the saw guide and drill guide in their coupled state illustrating the positioning of the first, second and third screw holes and the multiplicity of drill holes relative to each other;

FIG. 2E is a bottom view of the saw guide and drill guide in their coupled state illustrating the positioning of the transverse slot, the spacer, the first and second reams in the saw guide and the multiplicity of drill holes in the drill guide relative to each other;

FIG. 3 is an isolated elevational view of the drill guide showing the pins extending outward from the mounting end and the angular relationship of the multiplicity of drill holes in the drill guide;

FIGS. 4A and 4B are various side elevational views of the saw guide showing the first, second and third screw holes, the first and second reams, the transverse slot and the spacer in their relative positions to each other;

FIGS. 5A and 5B are a top plan view and a side elevational view, respectively, of the rigid plate showing the relative positions of the first, second, third, fourth and fifth securing holes therein;

FIGS. 6A and 6B are respective top plan and side elevational views of the distraction assembly showing the various parts therein in their relative positions to each other;

FIG. 10 is a side elevational view of the rigid plate in secured position on the one end and the other end of the bone illustrating the relative positioning of the first, second, third, fourth and fifth bone screws, as well as optional bone screws, to each other;

FIG. 12A is a top view of a new embodiment of the saw guide assembly having a plurality of equidistant reams formed therein across the width thereof;

FIG. 12B is a proximal end view of the new embodiment of the drill guide assembly of the invention having a plurality of positioning pins depending therefrom;

FIG. 12C is a proximal end view of the new embodiments of the saw guide assembly and the drill guide assembly assembled together to form a medial and lateral translation correction assembly allowing the drill guide assembly to be adjusted medially or laterally relative to the saw guide assembly;

FIGS. 13A–13C are side, proximal and distal end views of the new embodiment of the drill guide assembly having a supination and pronation correction assembly;

Similar reference characters refer to similar parts throughout the several views of the drawings.

DESCRIPTION OF THE PREFERRED EMBODIMENT

Figure 7A:
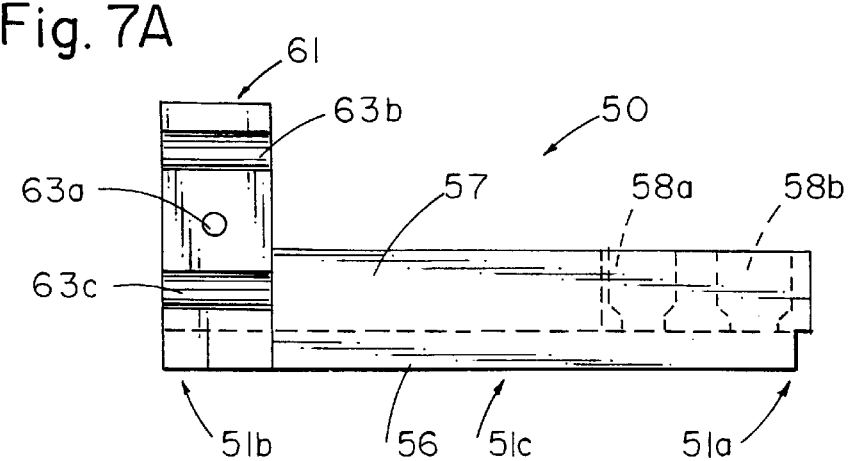
FIGS. 7A and 7B are side elevational views of the base frame of the distraction assembly showing the relative positioning of the first and second upstanding portions, the first and second blocks, and the first and second mounting holes in their relative positions to each other.

In referring to FIGS. 1 and 2A–E, the multi-plane bone distraction system is represented as comprising a saw guide means, a drill guide means and a multi-plane distraction means, generally indicated by numerals 10, 12 and 14, respectively. The multi-plane bone distraction system is to be used for repairing a bone 16 that has a malunion or fracture or for linear lengthening and shortening of the bone 16. The multi-plane bone distraction system provides for the performing of an osteotomy whereupon the bone 16 is cut thereby separating one end 16a from the other end 16b. The saw guide means 10 facilitates controlling the angle of sawing and sawing location on the bone 16 and the drill guide means 12 facilitates controlling the angle of drilling to apply to the other end 16b of the bone 16 and controlling the locations to drill on the other end 16b prior to sawing the bone 16. The saw guide means 10 and drill guide means 12 are also referred to herein as the saw guide 10 and the drill guide 12.

In referring now specifically to FIGS. 2A and 2B, various side views can be seen of the saw guide 10 and drill guide 12 in their coupled state. The saw guide 10 is comprised of a base structure 18 having a first end 19 and a second end 20. The base structure 18 further includes an upstanding wall 22 positioned about the perimeter of the base structure 18. The upstanding wall 22 is continuous at the second end 20 and open at the first end 19. Positioned adjacent the first end 19 is a first screw hole 24a and positioned intermediate to said first and second ends 19 and 20 is a second and third screw hole 24b and 24c. The first, second and third screw holes 24a, 24b and 24c, extend through the base structure 18.

Positioned adjacent the second end 20 and extending into the upstanding wall 22 are first and second reams 26a and 26b, respectively. The first and second reams 26a and 26b facilitate the coupling of the drill guide 12 to the saw guide 10. Further included on the base structure 18 is an integral thin wall 28 that extends outwardly as well as transversely from the second end 20 to form a transverse slot 30 therein. The transverse slot 30 is sized to receive a saw blade therein to thereby facilitating obtaining a precision cut in the bone 16. Additionally, extending outward from the integral thin wall 28 adjacent the second end 20 is a spacer 32. The spacer 32 facilitates sufficiently placing the transverse slot 30 at a safe distance from the radial-carpal articulation on the other end 16b of the bone 16 and at the preferred position to cut the bone 16, as when performing an osteotomy on the radius bone. By insuring the placement of the cut at a specified distance from the radial-carpal articulation, its integrity as a pivotal joint is preserved due to any subsequent drilling being located sufficiently away from the radial-carpal articulation. The saw guide 10 is preferably formed from a metallic heat-tolerable material, such as stainless steel, so to allow for high temperature sterilization as well as rigid structural strength.

In referring to FIGS. 2B, 2D and 2E, a side, top and bottom view respectively of the assembled saw guide 10 and drill guide 12 is further illustrated. The base structure 18 can be seen to have a longitudinal axis whereupon the first, second and third screw holes 24a, 24b and 24c are centrally aligned thereby. Further, FIG. 2E illustrates the relative spacing between the first and second reams 26a and 26b extending into the upstanding wall 22.

In referring now to FIGS. 2A, 2B, 2D, and 3, the drill guide 12 is illustrated as well. The drill guide is comprised of a main body 34 of generally an arcuate shape. The main body 34 includes a mounting end 36 having pins 37a and 37b coupled to and extending outward therefrom. The pins 37a and 37b are preferably fitted into the mounting end 36 (see FIG. 3). The main body 34 also includes a multiplicity of drill holes, generally indicated by numeral 38, that are angularly aligned in two planes and extend through the main body 34.

In referring specifically to FIGS. 2C and 3, the drill guide 12 is illustrated with the pins 37a and 37b shown extending outward from the mounting end 36. Further, the angularly-aligned relation of the drill holes 38 can be seen as spaced apart in the main body 34 (see FIG. 2C). The drill holes 38 are incrementally positioned at five degrees from one another creating an angular drilling range of plus or minus thirty (+/–30) degrees. The drill holes 38 are sized to loosely receive a 3.5 millimeter drill bit. The drill guide 12 is preferably formed from a structurally rigid heat-tolerable material, such as stainless steel. Similar to the saw guide 10, the drill guide 12 must be capable of tolerating high temperature sterilization.

In referring to FIGS. 4A and 4B, the saw guide 10 is further shown depicting the spaced relationship of the first and second reams 26a and 26b, the transverse slot 30 and the first, second and third screw holes 24a, 24b and 24c.

In referring now back to FIG. 1, the multi-plane distraction means 14 is shown to comprise a rigid plate 40 and a distraction assembly 48. The rigid plate 40 is shown in position on the bone 16 with the distraction assembly 48 seated on the rigid plate 40 and secured to the bone 16.

The rigid plate 40 can be seen in more detail in referring now to FIGS. 5A and 5B providing top and side views thereof. The rigid plate 40 is comprised of an elongated member 42 having a proximal end 42a and a distal end 42b. A first securing hole 44a is positioned adjacent the proximal end 42a. The first securing hole 44a comprises a slotted hole. Integral with and extending outward from the distal end 42b is an enlarged head 46. Positioned within the enlarged head 46 is a second, third and fourth securing hole 44b, 44c and 44d, respectively. The third and fourth securing holes 44b and 44c are formed asymmetrically so to initiate the divergence of screws inserted therethrough. A fifth securing hole 44e is positioned intermediate to the distal end 42b and the first securing hole 44a on the elongated member 42. The first, second, third, fourth and fifth securing holes 44a–44e are preferably countersunk. Further, the second, third and fourth securing holes 44b, 44c and 44d are preferably triangularly-spaced about the enlarged head 46. The rigid plate 40 is preferably formed from a structurally rigid heat-tolerable material, such as stainless steel. A heat-tolerable material is required so to facilitate high temperature sterilization as is similarly required for the saw guide 10 and drill guide 12. It is also preferable that the rigid plate 40 have a smooth polished surface.

In now referring specifically to FIGS. 6A and 6B, the distraction assembly 48 can be seen in more detail. FIG. 6A depicts the distraction assembly 48 in a top plan view and FIG. 6B depicts the distraction assembly 48 in a side elevational view. The distraction assembly 48 is comprised of a base frame 50, a multi-plane adjustment means generally indicated by reference numeral 52 and an adjustment head 54. The base frame 50 has one end 51a, an opposite end 51b and an underside 51c. Positioned on the underside 51c is a groove 56. The groove 56 has a cross-sectional configuration similar to the cross-sectional configuration of the elongated member 42 of the rigid plate 40 so to facilitate the base frame 50 being seated thereon.

The base frame 50, being elongated in shape and having a longitudinal axis, includes a slot 57 extending centrally from the opposite end 51b along the longitudinal axis to an intermediate point between the one end 51a and the opposite end 51b. The slot 57 being open at the opposite end 51b of the base frame 50. The slot 57 facilitates accessing the slotted hole 44a in the rigid plate 40 when the base frame 50 is seated on the rigid plate 40. Additionally, intermediate to the one end 51a and the slot 57, first and second mounting holes 58a and 58b, respectively, are positioned. The first and second mounting holes 58a and 58b are positioned so as to align with the slotted hole 44a of the rigid plate 40 when the base frame 50 is seated on the rigid plate 40.

Figure 7B:
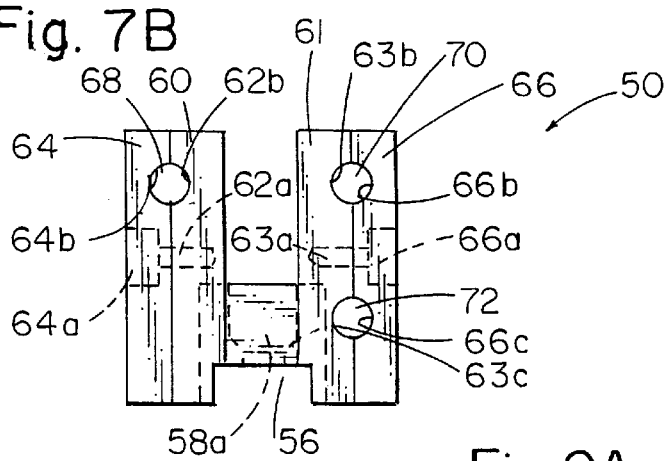

In referring now to FIGS. 7A and 7B, the base frame 50 can be seen in greater detail. The base frame 50 further includes first and second upstanding portions 60 and 61, respectively. The first upstanding portion 60 includes a first threaded transverse hole 62a and a first threaded circular groove 62b. The second upstanding portion 61 includes a second threaded transverse hole 63a, a second threaded circular groove 63b and a third threaded circular groove 63c. Secured to the first and second upstanding portions 60 and 61 are a first and second block 64 and 66, respectively. The first block 64 is sized to conform with the first upstanding portion 60 and includes a first countersunk transverse hole 64a and a fourth threaded circular groove 64b (see FIG. 7B). The second block 66 is sized to conform to the second upstanding portion 61 and includes a second countersunk transverse hole 66a, a fifth threaded circular groove 66b and a sixth threaded circular groove 66c.

The first countersunk hole 64a and the fourth threaded circular groove 64b are positioned on the first block 64 such that they cooperatively align with the respective first threaded transverse hole 62a and the first threaded circular hole 62b when the first block 64 is secured to the first upstanding portion 60. Likewise, the second countersunk transverse hole 66a, the fifth threaded circular groove 66b and the sixth threaded circular groove 66c cooperatively align with the respective second threaded transverse hole 63a, the second threaded circular groove 63b and the third threaded circular groove 63c when the second block 56 is secured to the second upstanding portion 61. The first block 64 is secured to the first upstanding portion 60 by way of installing a screw through the first countersunk transverse hole 64a into threaded engagement with the first threaded transverse hole 62a. Similarly, the second block 66 is secured to the second upstanding portion 61 by way of installing a screw through the second countersunk transverse hole 66a into threaded engagement with the second threaded transverse hole 63a.

Thus, after securing the first block 64 to the first upstanding portion 60, the first threaded circular groove 62b cooperates with the fourth threaded circular groove 64b to form a first threaded hole 68 which extends parallel to the longitudinal axis of the base frame 50. Similarly, when the second block 66 is secured in position on the second upstanding portion 61, the second threaded circular groove 63b and third threaded circular groove 63c cooperate with the respective fifth threaded circular groove 66b and the sixth threaded circular groove 66c so to form second and third threaded holes 70 and 72, respectively, that run parallel to the longitudinal axis of the base frame 50.

In referring now specifically back to FIG. 6A, the multi-plane adjustment means 52 can be seen in detail. The multi-plane adjustment means 52 is comprised of first, second and third adjustment screws 74, 76 and 78, respectively, of which each include a head portion, a ball member and a threaded shaft therebetween, a, b and c, respectively.

Figure 8:
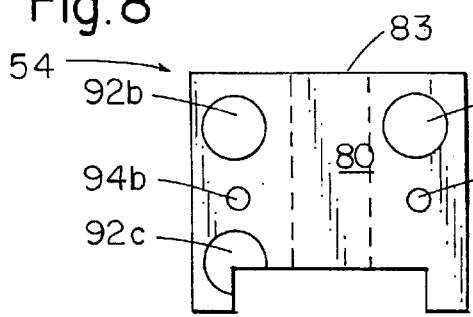
FIG. 8 is a backside elevational view of the adjustment head showing the first, second and third spherical sockets as well as the first and second threaded backside holes in their relative positions to each other.

In now referring to FIGS. 6A, 6B and 8, the adjustment head 54 can readily be understood. The adjustment head 54 has back, front, bottom and top sides 80, 81, 82 and 83, respectively. Protruding from the front side 81 is a pair of parallel columns 84a and 84b that extend transversely from the top side 83 to the bottom side 82 of the adjustment head 54. Each of the parallel columns 84a and 84b comprise a center bore 86a and 86b, respectively. Each of the center bores 86a and 86b further include inturned flanges 88a and 88b, respectively, positioned adjacent to the bottom side 82 thereby forming first and second recessed screw holes 90 and 91, respectively. The first and second recessed screw holes 90 and 91 are asymmetrically centered within the respective center bores 86a and 86b so to provide for an angled installation of mounting screws therethrough. Further, the adjustment head 54 includes a first and second lower extension 89a and 89b, respectively, protruding downward from the bottom side 82 of the adjustment head. The first and second lower extensions 89a and 89b facilitate gripping the other end 16b of the bone 16 when the adjustment head 54 is secured in place. The first and second extensions 89a and 89b also provide space between the bottom side 82 of the adjustment head 54 and the other end 16b of the bone 16 so that the rigid plate 40 can freely slide therebetween when the distraction assembly 48 is operated.

In referring now specifically to FIG. 8, the backside 80 of the adjustment head 54 can be seen to include first, second and third spherical sockets, 92a, 92b and 92c, respectively, positioned therein. Additionally, first and second threaded backside holes 94a and 94b, respectively, extend partially inward from the backside 80. The first threaded backside hole 94a is positioned intermediate to the first spherical socket 92a and the bottom side 82 of the adjustment head 54. Further, the second threaded backside hole 94b is positioned intermediate to the second and third spherical sockets 92b and 92c. The first, second and third spherical sockets 92a, 92b and 92c are sized to pivotally receive the ball members of the first, second and third adjustment screws 74, 76 and 78, respectively.

Figure 9A:
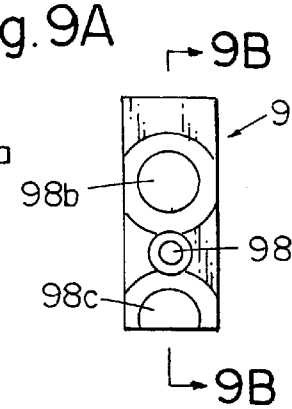
FIG. 9A is a front plan view of the second socket back member illustrating the second and third countersunk leveled holes and the second countersunk screw hole in their relative positions to each other.
Figure 9B:
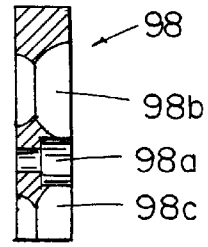
FIG. 9B is a cross-sectional view of the second socket back member taken along line B—B as depicted in FIG. 9A showing the second and third countersunk beveled holes and second countersunk screw hole in their relative positions to each other.

In referring to FIGS. 8, 9A and 9B, the adjustment head 54 and second back member 98 can be seen in detail. First and second back members 96 and 98, respectively, are secured to the back side 80 of the adjustment head 54 (see FIG. 6A). The first back member 96 includes a first countersunk beveled hole (not shown) and a first countersunk screw hole (not shown). Similarly, the second back member 98 includes a second countersunk screw hole 98a as well as a second and third countersunk beveled hole 98b and 98c, respectively (see FIGS. 9A and 9B). The first countersunk beveled hole on the first back member 96 is positioned so as to cooperatively align with the first spherical socket 92a on the back side 80 of the adjustment head 54 when the first back member 96 is secured thereto. The first back member 96 is secured to the adjustment head 54 by way of the installation of a screw through the first countersunk screw hole which is cooperatively aligned with the first threaded backside hole 94a.

Similarly, the second countersunk beveled hole 98b and the third countersunk beveled hole 98c on the second back member 98 are positioned so as to cooperatively align with respective second and third spherical sockets 92b and 92c on the back side 80 of the adjustment head 54 when the second back member 98 is secured thereto. The second back member 98 is secured to the backside 80 of the adjustment head 54 by way of the installing of a screw through the second countersunk screw hole 98a which is cooperatively aligned with the second threaded backside hole 94b. The first and second back members 96 and 98 serve to retain the ball members of the first, second and third adjustment screws 74, 76 and 78 within the respective first, second and third spherical sockets 92a, 92b and 92c.

The first, second, and third adjustment screws 74, 76 and 78 are threadedly received through the respective first, second and third threaded holes 68, 70 and 72 in the first and second upstanding portions 60 and 61 of the base frame 50. Thus, the first, second and third adjustment screws 74, 76 and 78 serve to interconnect the adjustment head 54 with the base frame 50 such that a clockwise rotation therein would produce an outward force on the adjustment head 54 and a counterclockwise rotation therein would produce an inward pulling force on the adjustment head 54. Therefore, by individually adjusting the first, second and third adjustment screws 74, 76 and 78, the adjustment head 54 may be repositioned relative to three planes.

In manufacturing the distraction assembly 48, it is preferably formed from a structurally rigid heat-tolerable material, such as stainless steel. A heat-tolerable material is required so to facilitate the high temperature sterilization thereof.

Now, having thusly described the structure and formation of the invention, its operation may be readily understood. The photographs of FIGS. 11A–11F illustrate the implementation of the various stages.

Figure 11A:
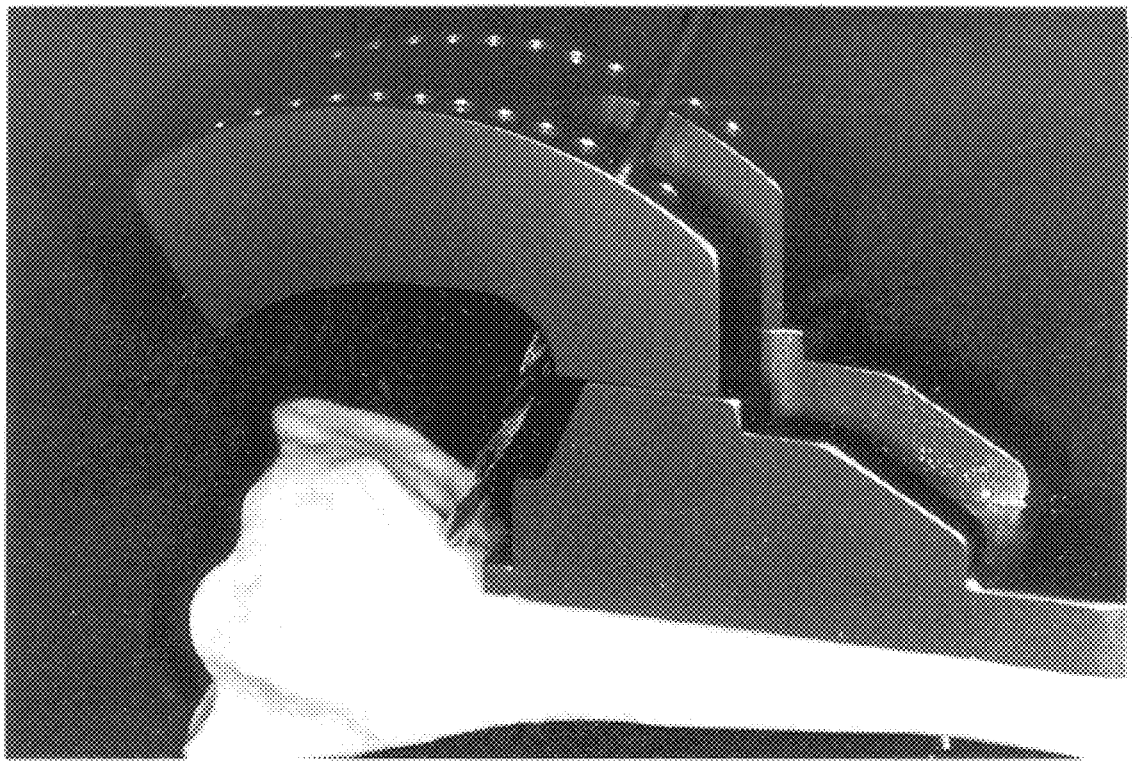
FIGS. 11A–11F are photographs of the multi-plane bone distraction system showing the sequential implementation thereof in performing an osteotomy.

As best illustrated in the photograph of FIG. 11A, the saw guide 10 is placed at the metaphysis adjacent the site of the cortical angulation (the abnormal bend in the cortex of the bone 16). It is imperative that the saw guide 10 not be placed too far toward the radial-carpal articulation (the other end 16b of the bone 16) so to insure against any interference with the radial-carpal joint. Next, the saw guide 10 is secured to the bone 16 by drilling three holes centered co-linearly with the longitudinal axis of the bone 16 with screws subsequently installed through said first, second and third screw holes 24a, 24b and 24c of the saw guide 10 into threaded engagement with the bone 16.

As further illustrated in the photograph of FIG. 11A, once the saw guide 10 is secured in position on the one end 16a of the bone 16, the drill guide 12 is coupled to the saw guide 10 by way of inserting the pins 37a and 37b of the drill guide 12 into the first and second reams 26a and 26b of the saw guide 10, respectively. Hence the main body 34 of the drill guide 12 will be extending outward overlying the radial-carpal articulation. Next, depending upon the degrees of correction required in the dorsal/volar plane to repair the malunion, a set of drill holes 38 are selected with which a drill bit is inserted therethrough and two holes are drilled in the other end 16b of the bone 16. The drill holes 38, angularly align in the main body 34 of the drill guide 12, are spaced apart in angular increments of five degrees. Thus, when the distraction assembly 48 is operated so to reposition the drilled holes perpendicular to the rigid plate 40, the desired degree of correction is achieved.

Figure 11B:
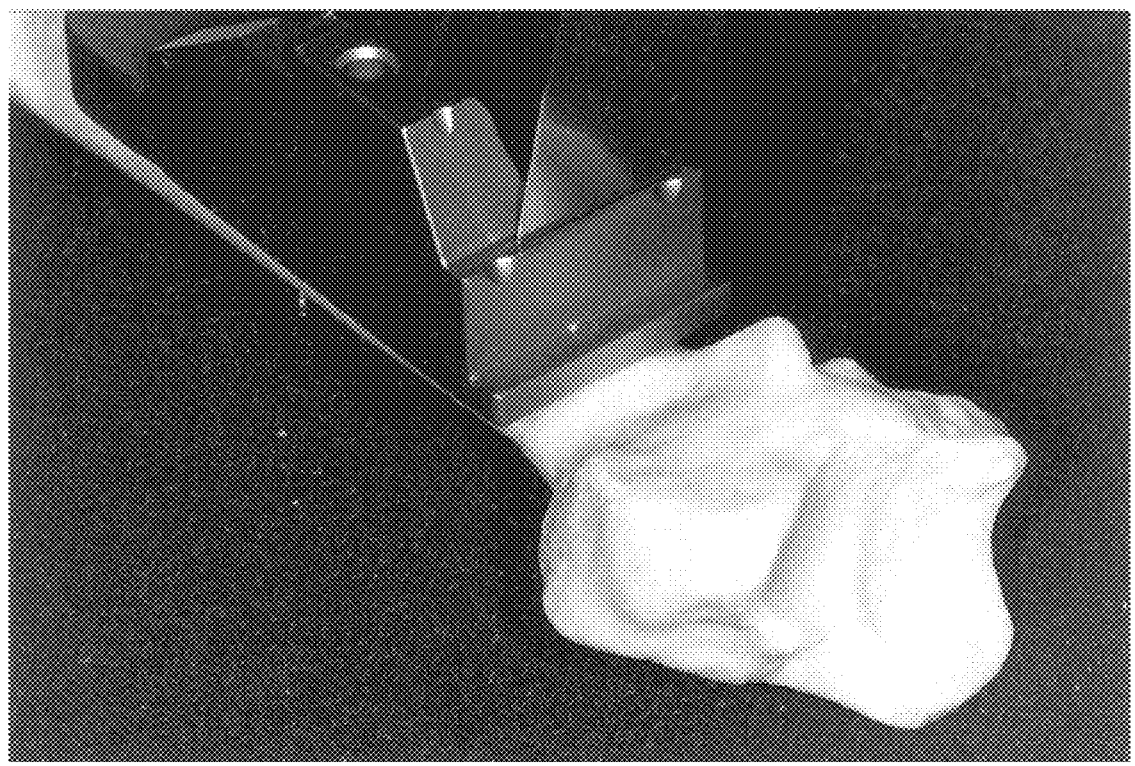

As best illustrated in the photograph of FIG. 11B, once the holes are drilled proximal to the radial-carpal articulation (the other end 16b of the bone 16), the drill guide 12 is removed from the saw guide 10. Next, the osteotomy is performed by inserting the saw blade through the transverse slot 30 and applying a side-to-side motion until the bone 16 is cut. Once the osteotomy is completed, the saw guide 10 is removed.

After removal of the saw guide 10, the rigid plate 40 is positioned on the one end 16a of the bone 16 and a first bone screw 100 is installed through the slotted hole 44a and threaded into the bone 16 by way of the hole formed in the bone 16 that corresponded to the second screw hole 24b of the saw guide 10 (see FIG. 1). Thus, the rigid plate 40 is slidably secured to the one end 16a of the bone 16 via the first bone screw 100.

Figure 11C:
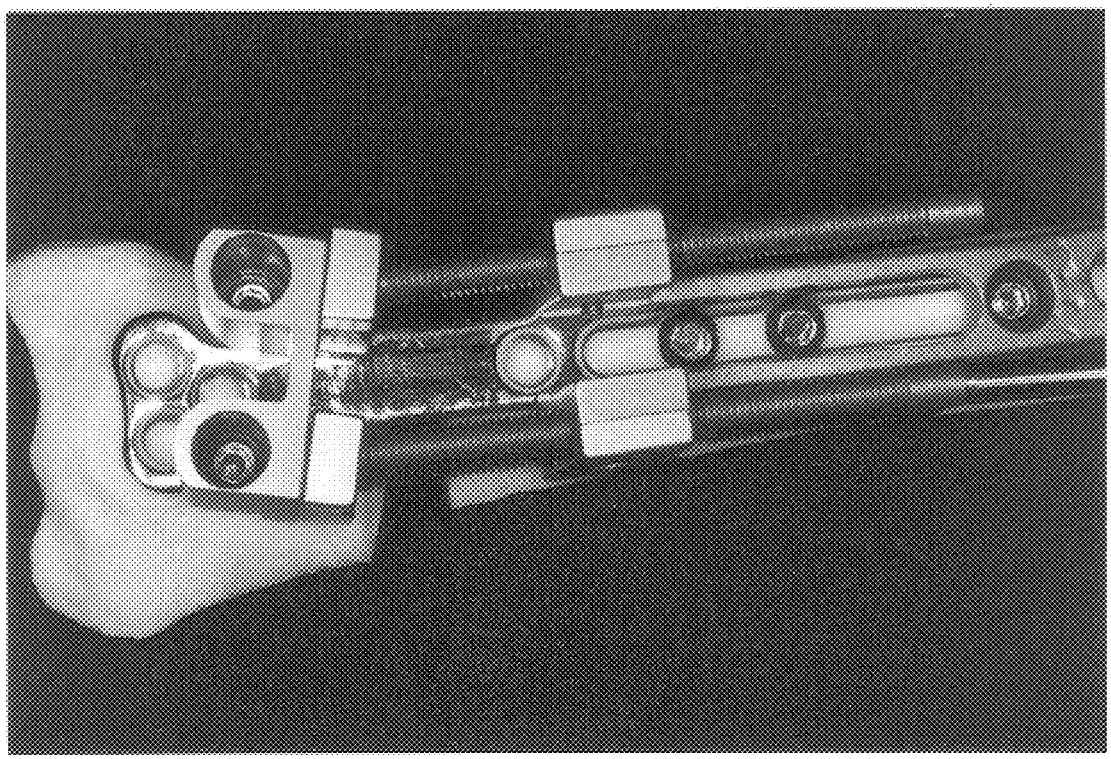
Figure 11D:
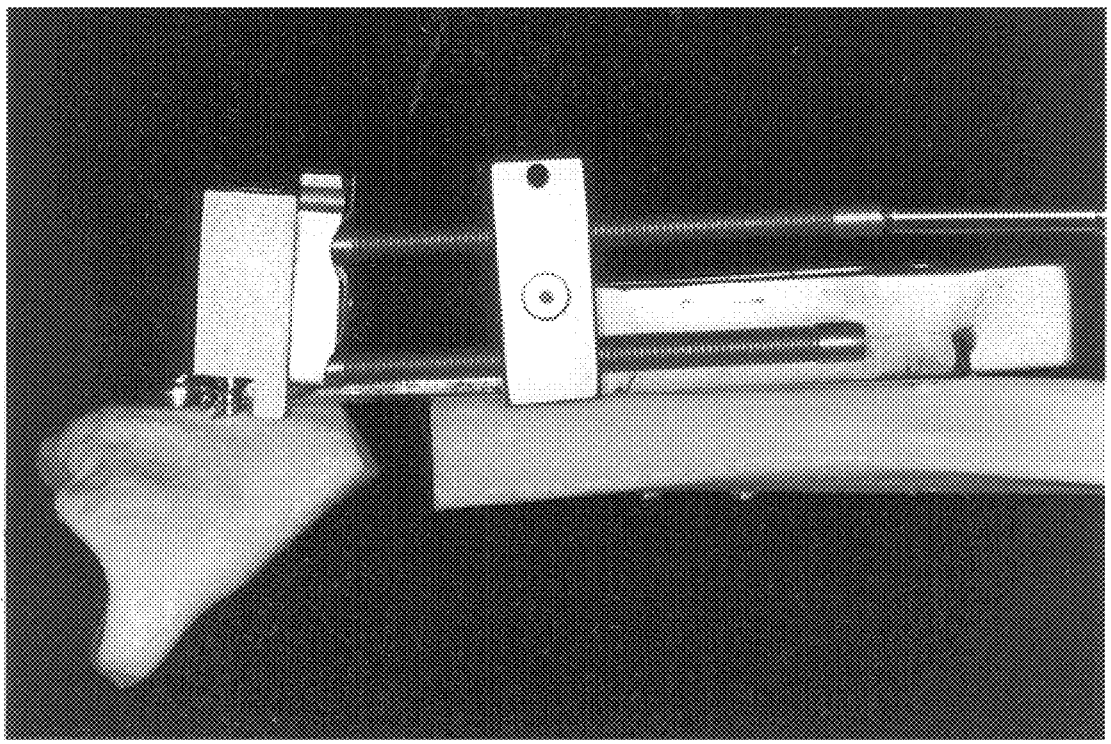

Next, as best illustrated in the photographs of FIGS. 11C and 11D, the base frame 50 of the distraction assembly 48 is seated on the rigid plate 40 such that a first mounting screw 101 is installed through the first mounting hole 58a in the base frame 50, through the slotted hole 44a of the rigid plate 40, and threaded into the hole in the bone 16 formed in correspondence to the first screw hole 24a of the saw guide 10 (see FIG. 1). The first mounting screw 101 will serve to secure both the distraction assembly 48 and the rigid plate 40 to the one end 16a of the bone 16. When applying the distraction assembly 48, the distraction assembly 48 should be in the fully-collapsed position with the adjustment head 54 positioned adjacent the upstanding portions 60 and 61 of the base frame 50.

Next, the adjustment head 54 is to be secured to the radial fragment (the other end 16b of the bone 16) by way of installing second and third mounting screws 102 and 103, respectively, through the first and second recessed screw holes 90 and 91 of the adjustment head 54 and threaded into the two pre-drilled corresponding holes in the radial fragment (the other end 16b of the bone 16). The second and third mounting screws 102 and 103 are to be sufficiently tightened to securely rest the radial fragment against the first and second lower extensions 89a and 89b which extend downward from the bottom side 82 of the adjustment head 54 (see FIG. 1). The rigid plate 40 is concurrently positioned between the second and third mounting screws 102 and 103 with the enlarged head 46 being positioned forward of the second and third mounting screws 102 and 103 such that during distraction adjustment the rigid plate 40 is forcibly slid outward in correspondence with the movement of the adjustment head 54.

Now that the distraction assembly 48 and rigid plate 40 are securely positioned to the one end 16a and the other end 16b of the bone 16, the first, second and third adjustment screws 74, 76 and 78 are to be gradually adjusted to first correct the length desired and then to correct for the angular tilt (radial/ulnar shown in FIG. 11C and volar/dorsal shown in FIG. 11D).

It is noted that upon tightening of the second and third mounting screws 102 and 103, the predicted angular tilt was automatically accounted for due to the holes in the radial-carpal articulation being initially drilled at the predicted angle. However, to correct for additional angular volar/dorsal tilt, the first and second adjustment screws 74 and 76 or the third adjustment screw 78 are then adjusted until the desired amount of angular tilt is achieved.

If a maximal distraction is required, additional length can be achieved by drilling an additional hole in the one end 16a of the bone 16 in alignment with the second mounting hole 58b positioned adjacent the one end 51a of the base frame 50. Next, a fourth mounting screw (not shown) is installed through the second mounting hole 58b and into threaded engagement with the one end 16a of the bone 16. Subsequent removal of the first mounting screw 101 is then required to allow the rigid plate 40 to slid to further facilitate additional distraction length. Upon sliding the rigid plate 40 distally toward the other end 16b of the bone 16, the hole corresponding to the third screw hole 24c of the saw guide 10 will become exposed through the slotted hole 44a of the rigid plate 40. An optional bone screw 109 can then be threaded into such exposed hole to further stabilize the rigid plate 40. Hence, the first bone screw 100 and the optional bone screw 109, installed through the slotted hole 44a, will be the only bone screws securing the rigid plate 40 to the bone 16 during adjustment under maximum distraction conditions.

Figure 11E:
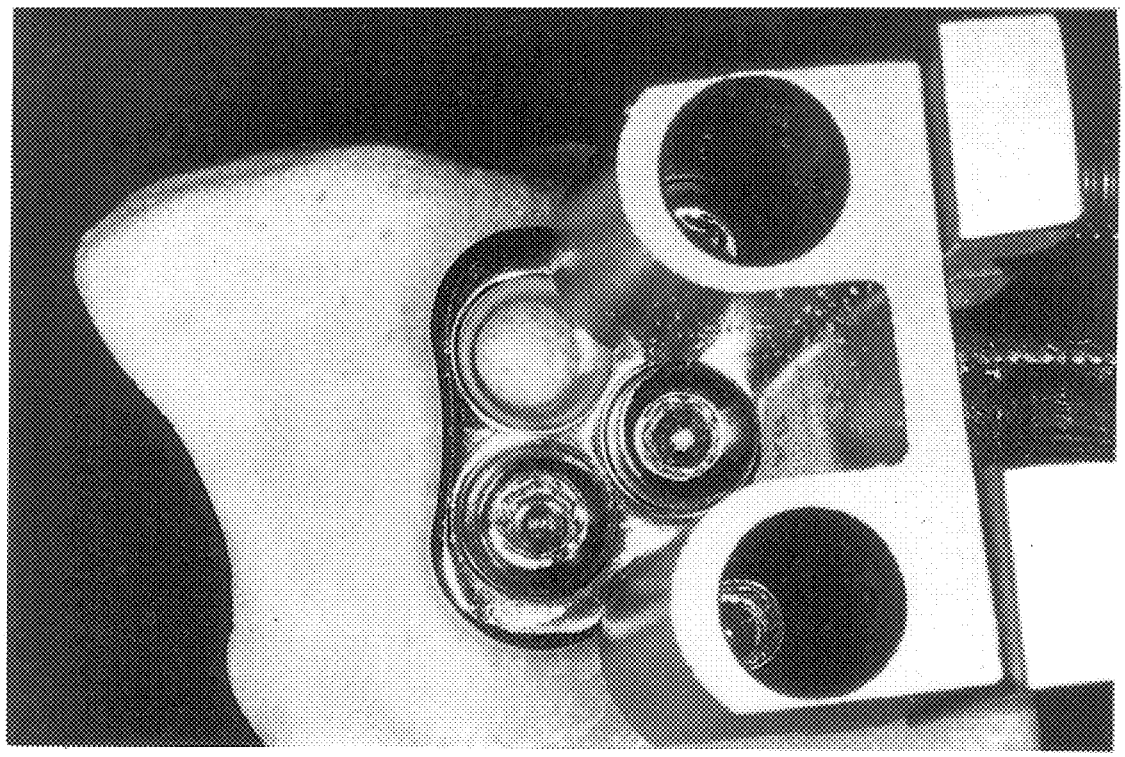

After adjusting the distraction assembly 48 to achieve the desired distraction length, radial/ulnar angulation and volar/dorsal tilt, the rigid plate 40 is secured in position on both the other end 16b and the one end 16a of the bone 16 (see FIG. 10 and the photograph of FIG. 11E). First, the first bone screw 100 is sufficiently tightened to prevent the rigid plate 40 from sliding and the other end 16b of the bone 16 is to have three holes drilled therein corresponding to the second, third and fourth securing holes 44b, 44c and 44d of the enlarged head 46. It is preferable that the drilled holes corresponding to the second, third and fourth securing holes 44b, 44c and 44d are to be drilled in a divergent nature so to assure a maximum securement. Although divergence is desired for maximum securement, the radial-ulnar joint or radial-carpal joint must not experience any screw intrusion. Next, a second, third and fourth bone screw 105, 106 and 107, respectively, are installed through the respective second, third and fourth securing holes 44b, 44c and 44d and threaded into the three divergently-drilled holes of the radial fragment (the other end 16b of the bone 16) until sufficiently secure. The third and fourth bone screws 106 and 107 diverge outward from each other while remaining aligned in the same plane.

Figure 11F:
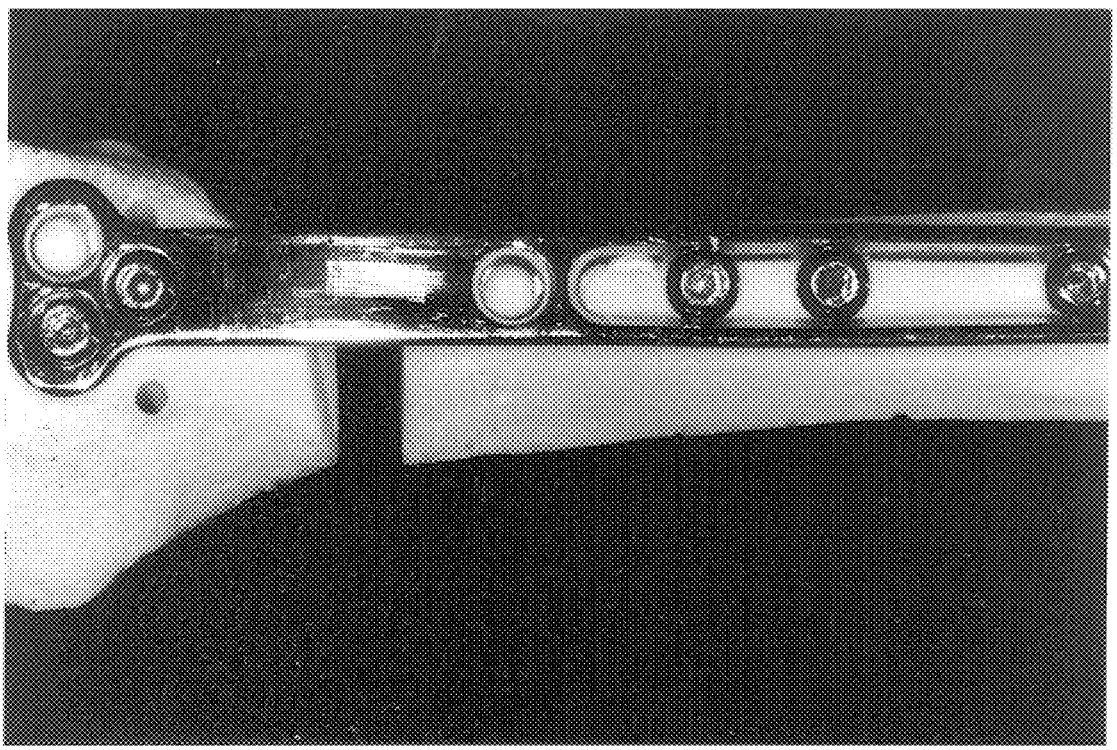

Finally, a fifth bone screw 108 is installed through the fifth securing hole 44e in the rigid plate 40 and threaded into both cortices of the one end 16a of the bone 16. Thereafter, the first, second and third mounting screws 101, 102 and 103 are removed from the one end 16*a* and the other end 16*b* of the bone 16 and the distraction assembly 48 is removed to thereby leave the rigid plate 40 securely in place fixing the other end 16*b* (radial fragment) in an adjusted position relative to the one end 16*a* of the bone 16. FIG. 10 and the photograph of FIG. 11F illustrate the rigid plate 40 in secured position after removal of the distraction assembly 48. It is noted that FIG. 1 illustrates the rigid plate 40 and the distraction assembly 48 in position after an adjustment has been effectuated and before the rigid plate 40 is secured by way of the second, third, fourth and fifth bone screws 105, 106, 107 and 108. Further, as illustrated in FIG. 10, optional bone screws 109, 110 and 111 can be installed through the slotted hole 44*a* of the rigid plate 40 into threaded engagement with the one end 16*a* of the bone 16 to insure maximum fixation of the rigid plate 40 to the one end 16*a* of the bone 16.

It is to be noted that bone graft insertion is possible before the insertion of the bone screws 105–108 and removal of the distraction assembly 48 by inserting a bone segment within the distracted gap and subsequently collapsing the distraction assembly 48 so as to compress the bone segment between the one end 16*a* and the other end 16*b* of the bone 16 (bone graft insertion not shown). After collapsing the distraction assembly 48 so as to compress the grafted bone segment, the rigid plate 40 is then secured in position via the second, third, fourth and fifth bone screws 105, 106, 107 and 108 in a similar fashion as described above.

It is to be further noted that in attempts to correct plane angulation (volar/dorsal tilt), it may be first required to adjust the distraction assembly 48 so as to preliminarily extend the adjustment head 54 out away from the base frame 50 before the other end 16*b* (radial fragment) of the bone 16 is secured to the adjustment head 54. This will avoid having the cortices of the one end 16*a* and the other end 16*b* of the bone 16 coming into contact with each other to thereby cause a fulcrum effect.

Since the filing of the parent patent application to this patent application, several modifications have been made to the distraction system. These modifications are illustrated in FIGS. 12–15.

As shown in FIG. 12A, the new embodiment of the saw guide assembly 10 of the invention includes two rows of a plurality of reams 26 formed therein across the width thereof. The reams 26 of each row are equidistantly spaced and are of the same diameter. As shown in FIG. 12B, the new embodiment of the drill guide assembly 12 of the invention includes a single row of a plurality of positioning pins 37 depending from its main body 34. The pins 37 are equidistantly spaced apart by the same distance as the reams 26 and are of the same diameter as the reams 26 so as to slidably fit therein. As shown in FIG. 12C, the new embodiments of the saw guide assembly 10 and the drill guide assembly 12 assembled together to form a medial and lateral translation correction assembly 100 allowing the drill guide assembly 12 to be adjusted medially or laterally relative to the saw guide assembly 10.

Figure 13B:
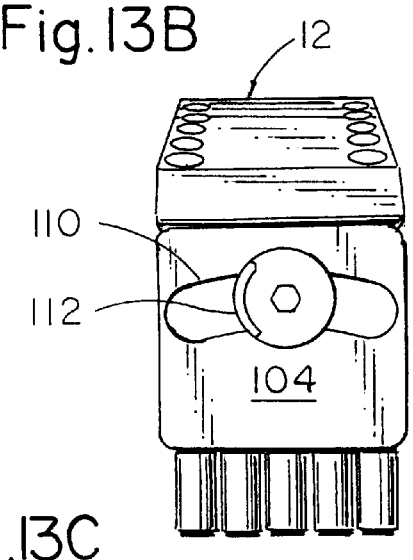
Figure 13D:
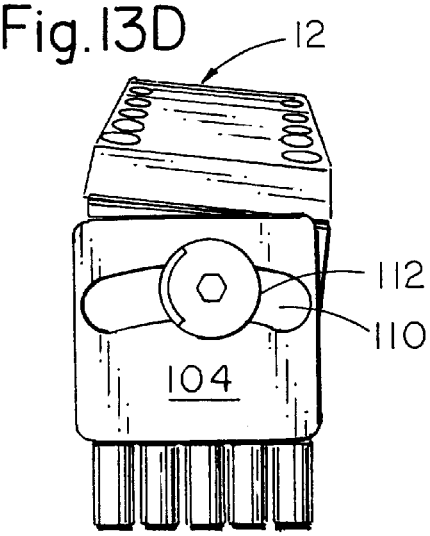
FIGS. 13D–13E are proximal and distal end views thereof showing the adjustability of the supination and pronation correction assembly.
Figure 13C:
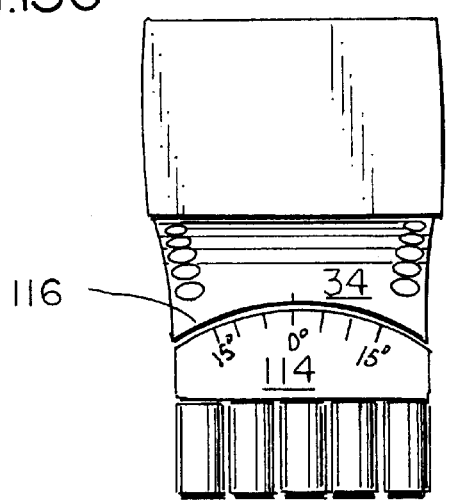
Figure 13E:
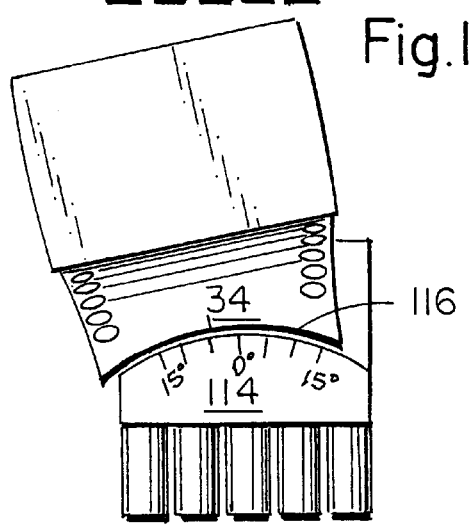
Figure 15A:
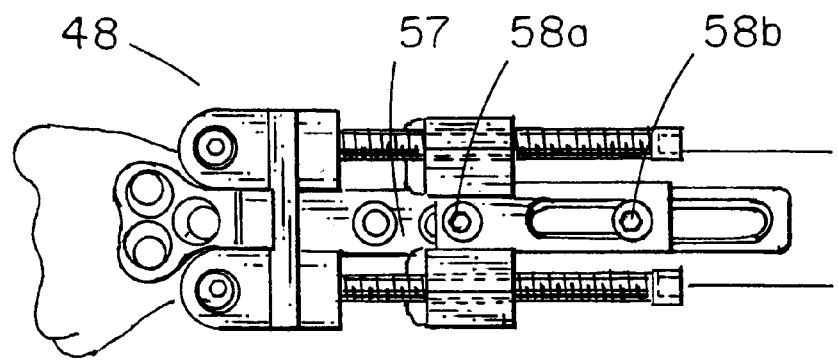
FIG. 15A is top plan view of the new embodiment of the distraction assembly modified to fit the new rigid plate as shown in FIG. 15B.
Figure 15B:
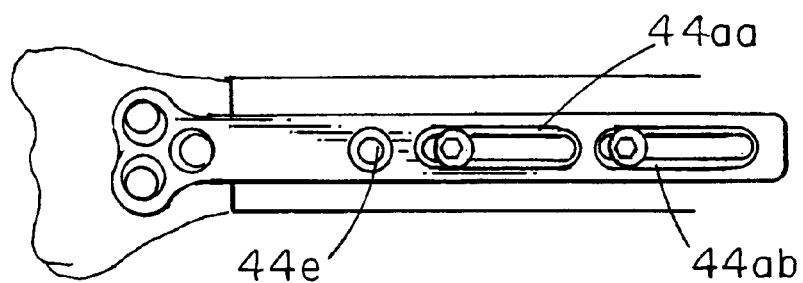

Turning now to FIGS. 13A–13C, the new embodiment of the drill guide assembly 12 also includes a supination and pronation correction assembly 102. The supination and pronation correction assembly 102 includes an L-shaped pivot bracket 104 having a proximal upstanding plate 106 and a lower humped plate 108. As best shown in FIG. 13B, the upstanding plate 13B includes an arcuate slot 110 formed therethrough for receiving a set screw 112 threaded into the flat face of the main body 34 of the drill guide 12. As best shown in FIG. 13C, the humped plate 108 includes a concave hump 114 and the main body 34 includes a convex indentation 116, both having radii substantially equal to the radius of the arcuate slot 110 to allow supination and pronation correction adjustments as desired (see FIGS. 13D & 13E).

Figure 14:
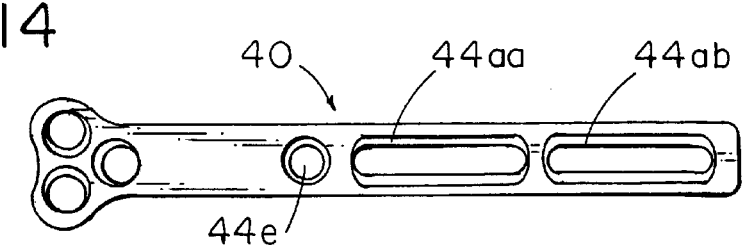
FIG. 14 is a top plan view of the new embodiment of the rigid plate.

As shown in FIG. 14, the new embodiment of the rigid plate 40 includes a pair of short slots 44*aa* & 44*ab* in lieu of the long slot 44*a* of the original embodiment (see FIG. 5*a*). Correspondingly, the new embodiment of the distraction assembly 48 is modified to fit the new rigid plate 40 with the slot 57 being minimized in length, the first hole 58*a* being moved distally and the second hole 58*b* being formed as a slot (see FIG. 15A as well as FIG. 15B with the distraction assembly removed).

The surgical protocol employing the new embodiments is very similar to the protocol described above in detail. However, for added clarity, reference is made to the Appendix hereof including the most-preferred surgical protocol, the disclosure of which is hereby incorporated by reference herein.

The present disclosure includes that contained in the appended claims, as well as that of the foregoing description. Although this invention has been described in its preferred form with a certain degree of particularity, it should be understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A multi-plane bone distraction system for use in distracting the ends of a bone and controlling the alignment thereof in three planes, said multi-plane bone distraction system comprising in combination:

a saw guide comprising a base structure for coupling to one end of the bone, said base structure having a longitudinal axis and a first and second end, at least one screw hole positioned through said base structure, and an integral wall extending outward from said second end forming a transverse slot, said transverse slot thereby facilitating the guided sawing of the bone;

a drill guide means for controlling the angle of drilling to apply to the other end of the bone and controlling the locations to drill on the other end of the bone, said drill guide means being coupled to said second end of said saw guide and thereby extending outward from said saw guide over the other end of the bone;

a multi-plane screw-driven distraction means for distracting and repositioning the other end of the bone in three planes from the one end of the bone to facilitate repairing the bone, said multi-plane distraction means being coupled to the one end and the other end of the bone after said saw guide and said drill guide means are removed from releasably secured positioning on the one end of the bone;

whereby said saw guide and said drill guide means may be positioned on the bone to facilitate the sawing and drilling of the bone whereupon said saw guide and said drill guide means are removed and said multi-plane distraction means may be positioned on the bone and operated allowing the other end of the bone to be distracted and repositioned in three planes relative to the one end of the bone.

2. The multi-plane bone distraction system as recited in claim 1, wherein said drill guide means is comprised of a main body having a mounting end, said main body further including a multiplicity of drill holes angularly aligned therein to thereby facilitate the guided drilling of the other end of the bone prior to sawing.

3. The multi-plane bone distraction system as recited in claim 2, wherein said saw guide further includes a spacer coupled to and extending outward from said second end, said spacer facilitating positioning said saw guide on the one end of the bone at a fixed distance from the other end.

4. The multi-plane bone distraction system as recited in claim 1, wherein said multi-plane distraction means is comprised of a rigid plate and a distraction assembly, said rigid plate being comprised of an elongated member having a proximal end, a distal end, a first securing hole positioned adjacent said proximal end, and an enlarged head coupled to said distal end, said first securing hole comprising a slotted hole, whereby said proximal end of said rigid plate may be coupled on the one end of the bone and said enlarged head may be coupled on the other end of the bone after said saw guide and said drill guide means are removed from releasably secured positioning on the one end of the bone, whereupon said distraction assembly is seated upon said proximal end of said rigid plate on said one end of the bone.

5. The multi-plane bone distraction system as recited in claim 4, wherein said enlarged head further includes a second, third and fourth securing hole positioned therethrough, and said elongated member further includes a fifth securing hole positioned intermediate to said distal end and said first securing hole.

6. The multi-plane bone distraction system as recited in claim 5, wherein said distraction assembly further includes a base frame seated on said proximal end of said rigid plate, said base frame having one end, an opposite end, a slot positioned centrally therebetween, an adjustment head having a first and a second recessed screw hole, and a multi-plane adjustment means for adjustably interconnecting said adjustment head to said base frame, said base frame further including a first mounting hole positioned at said one end.

7. The multi-plane bone distraction system as recited in claim 6, wherein said base frame further includes an underside and a groove positioned therein to facilitate said base frame being seated upon said rigid plate.

8. The multi-plane bone distraction system as recited in claim 6, wherein said multi-plane distraction means further includes a first mounting screw positioned through said first mounting hole of said base frame and said slotted hole of said rigid plate for coupling into the one end of the bone, a first bone screw positioned through said slotted hole of said rigid plate for coupling into the one end of the bone thereby slidably securing said rigid plate thereto, said centrally positioned slot in said base frame thereby providing access to said slotted hole, a second mounting screw positioned through said first recessed screw hole of said adjustment head for coupling into the other end of the bone, and a third mounting screw positioned through said second recessed screw hole of said adjustment head for coupling into the other end of the bone.

9. The multi-plane bone distraction system as recited in claim 8, wherein said distraction assembly further includes a second, third and fourth bone screw for positioning through said second, third and fourth securing holes in said enlarged head of said rigid plate, respectively, for coupling into the other end of the bone after said distracting assembly is operated.

10. The multi-plane bone distraction system as recited in claim 9, wherein said distraction assembly further includes a fifth bone screw positioned through said fifth securing hole in said elongated member of said rigid plate for coupling into the one end of the bone after said second and third mounting screws are removed from said adjustment head and said first mounting screw and said distraction assembly are removed from seated positioning on said rigid plate.

11. The multi-plane bone distraction system as recited in claim 6, wherein said base frame further includes a first and a second upstanding portion positioned at said opposite end, said first upstanding portion having a first threaded hole and said second upstanding portion having a second and a third threaded hole, said first, second and third threaded holes running parallel to the longitudinal axis of said base frame.

12. The multi-plane bone distraction system as recited in claim 11, wherein said adjustment head has a back side and further includes a first, a second and a third spherical socket positioned therein.

13. The multi-plane bone distraction system as recited in claim 12, wherein said multi-plane adjustment means is comprised of a first, a second and a third adjustment screw, each of said adjustment screws having a head portion, a ball member and a threaded shaft therebetween, said first, second and third adjustment screws being threaded through said first, second and third threaded holes in said first and second upstanding portions, respectively, and said ball members of said first, second and third adjustment screws being pivotally secured within said first, second and third spherical sockets, respectively, whereby said adjustment screws facilitate the adjusting of said adjustment head in three planes by being individually rotated clockwise to push outward on the adjustment head and rotated counter-clockwise to pull inward on said adjustment head.

14. The multi-plane bone distraction system as recited in claim 8, wherein said base frame further includes a second mounting hole positioned intermediate to said one end and said first mounting hole of said base frame, said second mounting hole allows for said first mounting screw to be removed from said first mounting hole and positioned therethrough into the one end of the bone so to facilitate said rigid plate further sliding outward when performing a large distraction.

15. A multi-plane screw-driven bone distraction system for use in distracting the ends of a bone and controlling the alignment thereof in three planes, said multi-plane bone distraction system comprising in combination:

a saw guide means for controlling the angle of sawing and sawing location on the bone, said saw guide means including means for coupling to the one end of the bone;

a drill guide comprised of a main body having a mounting end coupled to said saw guide means, said drill guide thereby extending outward from said saw guide means and over the other end of the bone, said drill guide including a multiplicity of drill holes angularly aligned therein to thereby facilitate the guided drilling of the other end of the bone prior to sawing;

a multi-plane distraction means for distracting and repositioning the other end in three planes from the one end of the bone to facilitate repairing the bone, said multi-plane distraction means being coupled to the one end and the other end of the bone after said saw guide and said drill guide means are removed from releasably secured positioning on the one end of the bone;

whereby said saw guide means and said drill guide may be positioned on the bone to facilitate the sawing and drilling of the bone whereupon said saw guide means and said drill guide are removed and said multi-plane distraction means may be positioned on the bone and operated allowing the other end of the bone to be distracted and repositioned in three planes relative to the one end of the bone.

16. The multi-plane bone distraction system as recited in claim 15, wherein said saw guide means is comprised of a base structure for coupling on one end of the bone, said base structure having a longitudinal axis and a first and second end, a first screw hole positioned at said first end and a second and third screw hole positioned intermediate to said first and second ends, and an integral wall extending outward from said second end forming a transverse slot, said transverse slot thereby facilitating the guided sawing of the bone.

17. The multi-plane bone distraction system as recited in claim 16, wherein said saw guide further includes a spacer for coupling to and extending outward from said second end, said spacer facilitating consistently positioning said saw guide on the one end of the bone at a fixed distance from the other end.

18. The multi-plane bone distraction system as recited in claim 15, wherein said multi-plane distraction means is comprised of a rigid plate and a distraction assembly, said rigid plate being comprised of an elongated member having a proximal end, a distal end, a first securing hole positioned adjacent said proximal end, and an enlarged head coupled to said distal end, said first securing hole comprising a slotted hole, whereby said proximal end of said rigid plate may be coupled on the one end of the bone and said enlarged head may be coupled on the other end of the bone after said saw guide and said drill guide means are removed from releasably secured positioning on the one end of the bone, whereupon said distraction assembly is seated upon said proximal end of said rigid plate on said one end of the bone.

19. The multi-plane bone distraction system as recited in claim 18, wherein said enlarged head further includes a second, third and fourth securing hole positioned therethrough, and said elongated member further includes a fifth securing hole positioned intermediate to said distal end and said first securing hole.

20. The multi-plane bone distraction system as recited in claim 19, wherein said distraction assembly further includes a base frame seated on said proximal end of said rigid plate, said base frame having one end, an opposite end, a slot positioned centrally therebetween, an adjustment head having a first and a second recessed screw hole, and a multi-plane adjustment means for adjustably interconnecting said adjustment head to said base frame, said base frame further including a first mounting hole positioned at said one end.

21. The multi-plane bone distraction system as recited in claim 20, wherein said base frame further includes an underside and a groove positioned therein to facilitate said base frame being seated upon said rigid plate.

22. The multi-plane bone distraction system as recited in claim 20, wherein said multi-plane distraction means further includes a first mounting screw positioned through said first mounting hole of said base frame and said slotted hole of said rigid plate for coupling into the one end of the bone, a first bone screw positioned through slotted hole of said rigid plate for coupling into the one end of the bone thereby slidably securing said rigid plate thereto, said centrally positioned slot in said base frame thereby providing access to said slotted hole, a second mounting screw positioned through said first recessed screw hole of said adjustment head for coupling into the other end of the bone, and a third mounting screw positioned through said second recessed screw hole of said adjustment head for coupling into the other end of the bone.

23. The multi-plane bone distraction system as recited in claim 22, wherein said distraction assembly further includes a second, third and fourth bone screw for positioning through said second, third and fourth securing holes in said enlarged head of said rigid plate, respectively, for coupling into the other end of the bone after said distracting assembly is operated.

24. The multi-plane bone distraction system as recited in claim 23, wherein said distraction assembly further includes a fifth bone screw positioned through said fifth securing hole in said elongated member of said rigid plate for coupling into the one end of the bone after said second and third mounting screws are removed from said adjustment head and said first mounting screw and said distraction assembly are removed from seated positioning on said rigid plate.

25. The multi-plane bone distraction system as recited in claim 20, wherein said base frame further includes a first and a second upstanding portion positioned at said opposite end, said first upstanding portion having a first threaded hole and said second upstanding portion having a second and a third threaded hole, said first, second and third threaded holes running parallel to the longitudinal axis of said base frame.

26. The multi-plane bone distraction system as recited in claim 25, wherein said adjustment head has a back side and further includes a first, a second and a third spherical socket positioned therein.

27. The multi-plane bone distraction system as recited in claim 26, wherein said multi-plane adjustment means is comprised of a first, a second and a third adjustment screw, each of said adjustment screws having a head portion, a ball member and a threaded shaft therebetween, said first, second and third adjustment screws being threaded through said first, second and third threaded holes in said first and second upstanding portions, respectively, and said ball members of said first, second and third adjustment screws being pivotally secured within said first, second and third spherical sockets, respectively, whereby said adjustment screws facilitate the adjusting of said adjustment head in three planes by being individually rotated clockwise to push outward on the adjustment head and rotated counter-clockwise to pull inward on said adjustment head.

28. The multi-plane bone distraction system as recited in claim 22, wherein said base frame further includes a second mounting hole positioned intermediate to said one end and said first mounting hole of said base frame, said second mounting hole allows for said first mounting screw to be removed from said first mounting hole and positioned therethrough for coupling into the one end of the bone to facilitate said rigid plate further sliding outward when performing a large distraction.

29. A multi-plane bone distraction system for use in distracting the ends of a bone and controlling the alignment thereof in three planes, said multi-plane bone distraction system comprising in combination:

a saw guide means for controlling the angle of sawing and sawing location on the bone, said saw guide means including means for coupling to the one end of the bone;

a drill guide means for controlling the angle of drilling to apply to the other end of the bone and controlling the locations to drill on the other end of the bone prior to sawing the bone;

a rigid plate, said rigid plate including an elongated member having a proximal end, a distal end, a first securing hole positioned adjacent said proximal end, and an enlarged head coupled to said distal end, said enlarged head further including a second, third and fourth securing hole positioned therethrough, said elongated member further including a fifth securing hole positioned intermediate to said distal end and said first securing hole, said first securing hole comprising a slotted hole, said proximal end of said rigid plate for coupling on the one end of the bone and said enlarged head for coupling on the other end of the bone after said saw guide means and said drill guide means are removed from coupling on the one end of the bone;

a screw-driven distraction assembly including a base frame seated on said proximal end of said rigid plate, said base frame having one end, an opposite end, a slot positioned centrally therebetween, an adjustment head having a first and a second recessed screw hole, and a multi-plane adjustment means for adjustably interconnecting said adjustment head to said base frame, said base frame further including a first mounting hole positioned adjacent said one end;

a first mounting screw positioned through said first mounting hole of said base frame and said slotted hole of said rigid plate for coupling into the one end of the bone;

a first bone screw positioned through said slotted hole of said rigid plate and threaded into the one end of the bone thereby slidably securing said rigid plate thereto, whereby said centrally positioned slot in said base frame provides access to said slotted hole;

a second mounting screw positioned through said first recessed screw hole of said adjustment head for coupling into the other end of the bone;

a third mounting screw positioned through said second recessed screw hole of said adjustment head for coupling into the other end of the bone;

a second, third and fourth bone screw for positioning through said second, third and fourth securing holes in said enlarged head of said rigid plate, respectively, for coupling into the other end of the bone after said distracting assembly is operated;

a fifth bone screw positioned through said fifth securing hole in said elongated member of said rigid plate for coupling into the one end of the bone after said second and third mounting screws are removed from said adjustment head and said first mounting screw and said distracting assembly are removed from seated positioning on said rigid plate;

whereby said base frame may be rigidly secured in position on the one end of the bone with said rigid plate slidably secured therebetween and said distracting assembly operated allowing said rigid plate to slide relative to said first mounting screw and said first bone screw secured within said slotted hole, said rigid plate thereby sliding in response to movement in said adjustment head facilitating the distracting of the ends of the bone whereupon said first bone screw may be securely tightened and said second, third, fourth and fifth bone screws may be installed and then said first, second and third mounting screws and said base frame are removed and said first mounting screw reinstalled through said slotted hole.

30. The multi-plane bone distraction system as recited in claim 29, wherein said saw guide means is comprised of a base structure for coupling on one end of the bone, said base structure having a longitudinal axis and a first and second end, a first screw hole positioned at said first end and a second and third screw hole positioned intermediate to said first and second ends, and an integral wall extending outward from said second end forming a transverse slot, said transverse slot thereby facilitating the guided sawing of the bone.

31. The multi-plane bone distraction system as recited in claim 30, wherein said saw guide further includes a spacer coupled to and extending outward from said second end, said spacer facilitating consistently positioning said saw guide on the one end of the bone at a fixed distance from the other end.

32. The multi-plane bone distraction system as recited in claim 29, wherein said drill guide means is comprised of a main body having a mounting end, said main body further including a multiplicity of drill holes angularly aligned therein to thereby facilitate the guided drilling of the other end of the bone prior to sawing.

33. The multi-plane bone distraction system as recited in claim 29, wherein said base frame further includes an underside and a groove positioned therein to facilitate said base frame being seated upon said rigid plate.

34. The multi-plane bone distraction system as recited in claim 29, wherein said base frame further includes a first and a second upstanding portion positioned at said opposite end, said first upstanding portion having a first threaded hole and said second upstanding portion having a second and a third threaded hole, said first, second and third threaded holes running parallel to the longitudinal axis of said base frame.

35. The multi-plane bone distraction system as recited in claim 34, wherein said adjustment head has a back side and further includes a first, a second and a third spherical socket positioned therein.

36. The multi-plane bone distraction system as recited in claim 35, wherein said multi-plane adjustment means is comprised of a first, a second and a third adjustment screw, each of said adjustment screws having a head portion, a ball member and a threaded shaft therebetween, said first, second and third adjustment screws being threaded through said first, second and third threaded holes in said first and second upstanding portions, respectively, and said ball members of said first, second and third adjustment screws being pivotally secured within said first, second and third spherical sockets, respectively, whereby said adjustment screws facilitate the adjusting of said adjustment head in three planes by being individually rotated clockwise to push outward on the adjustment head and rotated counter-clockwise to pull inward on said adjustment head.

37. The multi-plane bone distraction system as recited in claim 29, wherein said base frame further includes a second mounting hole positioned intermediate to said one end and said first mounting hole of said base frame, said second mounting hole allows for said first mounting screw to be removed from said first mounting hole and positioned therethrough for coupling into the one end of the bone so to facilitate said rigid plate further sliding outward when performing a large distraction.

38. The distraction assembly as set forth in claim 15, further including means for one of medial and lateral translation correction adjustments.

39. The distraction assembly as set forth in claim 15, wherein said drill guide comprised of a main body having a mounting end coupled to said saw guide means comprises in combination a plurality of pins extending from said main body, at least some of which extend into a plurality of reams formed in said saw guide means, thereby facilitating at least one of medial or lateral correction adjustments.

40. The distraction assembly as set forth in claim 15, further including means for one of a supination and correction adjustments.

41. The distraction assembly as set forth in claim 15, wherein said drill guide includes an adjustment bracket interposed between said main body and said saw guide means, said adjustment bracket having a proximal plate with an arcuate slot for adjustable fixation to said main body by means of a fastener, said adjustment bracket being coupled to said saw guide means, thereby facilitating one of supination and pronation correction adjustments.

* * * * *